United States Patent
Chaudhari et al.

(10) Patent No.: US 6,858,753 B2
(45) Date of Patent: Feb. 22, 2005

(54) PROCESS FOR THE PREPARATION OF CARBOXYLIC ACIDS FROM ALIPHATIC ALCOHOLS

(75) Inventors: Raghunath Vitthal Chaudhari, Maharashtra (IN); Sunil Shankar Joshi, Maharashtra (IN); Ashutosh Anant Kelkar, Maharashtra (IN); Sunil Sadashiv Divekar, Maharashtra (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/097,141

(22) Filed: Mar. 14, 2002

(65) Prior Publication Data

US 2003/0176732 A1 Sep. 18, 2003

(51) Int. Cl.$^7$ ............... C07C 229/00; C07C 51/12; C07C 51/02; C07C 53/00; C07C 51/10
(52) U.S. Cl. ............... 562/519; 562/512; 562/517; 562/497; 562/406
(58) Field of Search ............... 562/519, 512, 562/517, 497, 406

(56) References Cited

U.S. PATENT DOCUMENTS 4,620,033 A * 10/1986 Isshiki et al. ............... 562/519

* cited by examiner

*Primary Examiner*—Elvis O. Price
(74) *Attorney, Agent, or Firm*—Nixon & Vanderhye P.C.

(57) ABSTRACT

The present invention provides an improved process for the production of carboxylic acids by the carbonylation of alcohol. The process involves contacting an alcohol with carbon monoxide in the presence of a nickel compound, a heterocyclic organic compound and an iodide promoter to produce the corresponding carboxylic acid. The improvement relates to the use of heterocyclic organic compound as a promoter containing at least two heteroatoms of which at least one is selected independently from S or N, which provides an inexpensive and stable catalyst system.

41 Claims, No Drawings

PROCESS FOR THE PREPARATION OF CARBOXYLIC ACIDS FROM ALIPHATIC ALCOHOLS

FIELD OF THE INVENTION

The present invention relates to a process for the preparation of carboxylic acids from aliphatic alcohols. More particularly, the present invention relates to a process for the conversion of aliphatic alcohols to carboxylic acids using a nickel containing catalyst.

BACKGROUND OF THE INVENTION

Carboxylic acids such as acetic acid are used in large quantities as basic chemicals for industrial purposes such as solvents, raw materials and intermediates in several reactions.

Various industrial processes are known for the preparation of carboxylic acids such as acetic acid. For example it is known to prepare carboxylic acid by the carbonylation of corresponding aliphatic alcohol, such as preparation of acetic acid by the carbonylation of methanol with carbon monoxide. The prior art discloses a number of catalysts for the preparation of carboxylic acid, particularly acetic acid, by carbonylation process. Generally, homogenous catalysts are used in carbonylation reactions.

German Patent Nos. 902495, 933148, 2303271 and 2400534 disclose the use of cobalt complex catalysts for the catalytic conversion of alcohols to carboxylic acids at temperatures in the range of 250 to 300° C. and pressure of from 680 t0 700 atmospheres. These high temperatures and pressures were necessary to stabilize the active catalytic species during the carbonylation reaction of for example, methanol to acetic acid. The processes of these disclosures also required complex separation processes and suffered from low selectivity to the final acid product.

French Patent No. 157313, South African Patent No. 68/2174 and U.S. Pat. Nos. 3,689,533 and 3,769,326 disclose the carbonylation of methanol using noble metals from Group VIII of the periodic table such as rhodium, iridium and platinum in the presence of bromine or iodine compounds as promoters. German Patent Nos. 1941449 and 1939286, British Patent No. 1233121, U.S. Pat. No. 3,816, 490 and South African Patent No. 68/2174 disclose the use of rhodium metal complex and iodine compound promoters in the carbonylation of methanol to acetic acid. These processes operate at lower pressures of carbon monoxide compared to the earlier processes using cobalt complex catalysts, and provide a better selectivity for acetic acid. U.S. Pat. No. 5,510,524, EP 728726A1, 752406A1, 849249A1 and 849250A1 disclose the use of iridium complex catalyst for the carbonylation of methanol to acetic acid. The catalyst system employed comprises an iridium catalyst, alkyl halide promoter and promoters such as rhenium, ruthenium, osmium, cadmium, mercury, zinc, gallium, indium and tungsten. These promoters were found to be beneficial in getting higher activity at lower water concentrations. However, the above processes use iridium and rhodium, which are expensive ingredients. The systems for recovery are extremely complex and increase the cost of the reaction.

U.S. Pat. Nos. 4,537,871; 4,540,811; 4,134,912 and 4,356,320 disclose processes for the carbonylation of methanol using nickel catalysts and iodide promoters along with triphenyl phosphine and promoters such as molybdenum, tungsten, chromium or tin compounds. These processes are carried out at lower temperatures and lower pressures. However, these processes show poor selectivity for acetic acid due to the formation of side products such as dimethyl ether and methane. As a result these processes are inferior when compared to earlier processes using rhodium catalysts. U.S. Pat. No. 4,902,659 discloses nickel complex catalyst with isoquinoline as a ligand. While a claim of high selectivity is made, the stability of the catalyst is not known.

OBJECTS OF THE INVENTION

The main object of the invention is to provide a economical and efficient catalytic process for the carbonylation of alcohols to carboxylic acids which overcomes the disadvantages of the prior art.

It is another object of the invention to provide a catalytic process for the preparation of carboxylic acids from the corresponding alcohols wherein the catalyst is prepared in situ and evinces high selectivity and yield of the carboxylic acid product.

SUMMARY OF THE INVENTION

The invention resides in the finding that the activity of a nickel catalyst is significantly enhanced when the catalyst is used in combination with a heterocyclic organic compound as a ligand or promoter. The heterocyclic organic compound contains at least two heteroatoms of which at least one is selected from S— or N—. An iodide promoter is also used.

Accordingly, the present invention provides a process for the preparation of a carboxylic acid from the corresponding aliphatic alcohol, said process comprising reacting a nickel source, an iodine source, and a ligand in a solvent under carbon monoxide atmosphere to obtain an in situ catalyst complex, contacting a mixture of aliphatic alcohol and carbon monoxide with said catalyst complex at a temperature in the range of 100 to 400° C. and a pressure in the range of 5 to 3000 psig, for a minimum of 30 minutes, and separating the product obtained.

In one embodiment of the invention, the alcohols used comprise aliphatic alcohols with 1 to 4 carbon atoms.

In another embodiment of the invention, the nickel source is selected from nickel and nickel salts selected from the group consisting of nickel chloride, nickel acetate, nickel bromikde and nickel iodide, and nickel powder.

In another embodiment of the invention, the iodide source is selected from the group consisting of alkyl iodide, hydroiodic acid and alkali metal iodide.

In a further embodiment of the invention, the alkyl iodide comprises methyl iodide.

In a further embodiment of the invention, the alkali metal iodide is selected from the group consisting of lithium iodide, sodium iodide and cesium iodide.

In yet another embodiment of the invention, the ligand comprises a heterocyclic organic compound containing at least two heteroatoms of which at least one is selected from S— and N—.

In a further embodiment of the invention, the heterocyclic compound is selected from the group consisting of morpholine, 1,4 thioxane, 2,2'bithiophene, thiamorpholine, thianthrene, 1,4 dithiane, 1,2-ethaneditiol and 2-mercapto pyridine.

In yet another embodiment of the invention, the catalyst complex is of the general formula $A_lB_mC_n$, wherein A is nickel, B is the ligand or promoter, C is the iodide promoter, l is the mole percentage of nickel and is in the range of 1 to 25, m is the mole percentage of ligand or promoter and is in the range of 5 to 50, and n is the mole percentage of the iodide promoter, such that m/l=2 to 8 and l+m+n=100.

In another embodiment of the invention, the solvent used comprises an aliphatic carboxylic acid.

In a further embodiment of the invention, the aliphatic carboxylic acid is selected from the group consisting of acetic acid, propionic acid and butyric acid.

In another embodiment of the invention, the mole ratio of the solvent to the alcohol is in the range of 0.5 to 10.

In another embodiment of the invention, the carbonylation reaction is carried out in the presence of water and hydrogen.

In a further embodiment of the invention, the amount of water is in the range of 5 to 10% of the total charge.

In another embodiment of the invention, the aliphatic alcohol used is methanol to obtain acetic acid and methyl acetate.

In yet another embodiment of the invention, the aliphatic alcohol used is ethanol to obtain propionic acid and ethyl propionate.

In another embodiment of the invention, the ratio of carbon monoxide to hydrogen in the pressurizing gas is from 1 to 40 preferably from 1 to 30.

In a further embodiment of the invention, the reactor is flushed with an inert gas such as nitrogen before the start of the reaction.

In another embodiment of the invention, the volatile iodide promoter and the carboxylic acid product are separated from the catalyst composite at the end of the reaction.

In a further embodiment of the invention, the volatile iodide promoter and the carboxylic acid product are separated from the catalyst composite by distillation.

In a further embodiment of the invention, the catalyst and the promoter are recycled for additional use.

DETAILED DESCRIPTION OF THE INVENTION

As explained above, the invention resides in the finding that the activity of a nickel catalyst is significantly enhanced when the catalyst is used in combination with a heterocyclic organic compound as a ligand or promoter. The heterocyclic organic compound contains at least two heteroatoms of which at least one is selected from S— or N—. An iodide promoter is also used. The present invention provides a process for the preparation of a carboxylic acid from the corresponding aliphatic alcohol, said process comprising reacting a nickel source, an iodine source, and a ligand in a solvent under carbon monoxide atmosphere to obtain an in situ catalyst complex, contacting a mixture of aliphatic alcohol and carbon monoxide with said catalyst complex at a temperature in the range of 100 to 400° C. and a pressure in the range of 5 to 3000 psig, for a minimum of 30 minutes, and separating the product obtained. The alcohols used generally comprise aliphatic alcohols with 1 to 4 carbon atoms, though higher alcohols can also be converted to the respective carboxylic acids using the process of the invention.

The nickel source is selected from nickel and nickel salts selected from the group consisting of nickel chloride, nickel acetate, nickel bromikde and nickel iodide, and nickel powder and the iodide source is selected from the group consisting of alkyl iodide such as methyl iodide, hydroiodic acid and alkali metal iodide such as lithium iodide, sodium iodide and cesium iodide. The ligand comprises a heterocyclic organic compound containing at least two heteroatoms of which at least one is selected from S— and N— such as morpholine, 1,4 thioxane, 2,2'bithiophene, thiamorpholine, thianthrene, 1,4 dithiane, 1,2-ethaneditiol and 2-mercapto pyridine.

The catalyst complex is of the general formula $A_l B_m C_n$, wherein A is nickel, B is the ligand or promoter, C is the iodide promoter, l is the mole percentage of nickel and is in the range of 1 to 25, m is the mole percentage of ligand or promoter and is in the range of 5 to 50, and n is the mole percentage of the iodide promoter, such that m/l=2 to 8 and l+m+n=100. The solvent used comprises an aliphatic carboxylic acid such as acetic acid, propionic acid and butyric acid. It is a feature of the invention that mono-carboxylic acids such as acetic acid, or propionic acid are used as solvents. The mole ratio of the solvent to the alcohol is preferably in the range of 0.5 to 10. The carbonylation reaction can be carried out in the presence of water and hydrogen. When water is present in the reactor, the amount of water is in the range of 5 to 10% of the total charge.

In a feature of the invention, the aliphatic alcohol used is methanol to obtain acetic acid and methyl acetate and ethanol to obtain propionic acid and ethyl propionate. The reaction can be conveniently carried out in a stirred pressure reactor with the improved catalyst used in homogeneous phase with a suitable solvent. The solvent can be a mono-carboxylic acid such as acetic acid or propionic acid. The process is capable of tolerating the presence of carbon monoxide gas used for the pressurization of impurities such as hydrogen, nitrogen, carbon dioxide without adversely affecting the carbonylation reaction. In fact, the presence of hydrogen is found to be beneficial to achieve high activity and selectivity for the prepared catalysts. The ratio of carbon monoxide to hydrogen in the pressurizing gas can be from 1 to 40 preferably from 1 to 30. The reactor can be flushed with an inert gas such as nitrogen before the start of the reaction for reasons of safety. After the completion of the reaction, the volatile iodide promoter and the carboxylic acid product are separated from the catalyst composite in any known manner such as distillation. The catalyst and the promoter can be recycled for additional use while the crude carboxylic acid is processed further to purify it.

The process of the invention is described below with illustrative examples. The examples should not be construed as limiting the scope of the invention in any manner.

EXAMPLE 1

A 300 ml stirred autoclave was charged with the following compounds including the reactant and the catalyst components:

| | |
|---|---|
| Methanol | 0.5 moles |
| Methyl iodide | 0.08 moles |
| $Ni(OAc)_2 \cdot 4H_2O$ | 0.0084 moles |
| Water | 0.166 moles |
| Acetic acid (solvent) | 1.25 moles |

The contents of the autoclave were flushed with nitrogen and then with carbon monoxide. The contents were heated to 225° C. and the autoclave was pressurized with hydrogen (5% of total pressure) and carbon monoxide to a total pressure of 1000 psig. There was no pressure drop in the reactor even after 60 minutes reaction time. The GC analysis did not show any acetic acid formation in this reaction. This indicates that nickel acetate and methyl iodide do not form active catalyst complex.

The following examples show the role of ligand or promoter in the formation of active catalyst complex.

EXAMPLE 2

A 300 ml stirred autoclave was charged with the following compounds including the reactant and the catalyst components:

| | |
|---|---|
| Methanol | 0.5 moles |
| Methyl iodide | 0.08 moles |
| Ni(OAc)$_2$.4H$_2$O | 0.0084 moles |
| Morpholine | 0.0336 moles |
| Water | 0.166 moles |
| Acetic acid (solvent) | 1.25 moles |

The contents of the autoclave were flushed with nitrogen and then with carbon monoxide. The contents were heated to 225° C. and the autoclave was pressurized with hydrogen (5% of total pressure) and carbon monoxide to a total pressure of 1000 psig. The pressure in the autoclave was maintained constant at 1000 psig by supplying only carbon monoxide from reservoir. The progress of the reaction was monitored by observing the pressure drop in the carbon monoxide reservoir. The reaction was continued till the pressure drop stopped completely. The reactor was then cooled and the liquid phase was analyzed by gas chromatography (GC). After 62 minutes, the GC analysis showed 88.04% conversion with 96.1% selectivity to acetic acid.

EXAMPLE 3

A 300 ml stirred autoclave was charged with the following compounds including the reactant and the catalyst components:

| | |
|---|---|
| Methanol | 0.5 moles |
| Methyl iodide | 0.08 moles |
| Ni(OAc)$_2$.4H$_2$O | 0.0084 moles |
| Morpholine | 0.0336 moles |
| Acetic acid (solvent) | 1.25 moles |

The contents of the autoclave were flushed with nitrogen and then with carbon monoxide. The contents were heated to 225° C. and the autoclave was pressurized with hydrogen (5% of total pressure) and carbon monoxide to a total pressure of 1000 psig. The pressure in the autoclave was maintained constant at 1000 psig by supplying only carbon monoxide from reservoir. In this instance, carbon monoxide absorption commenced immediately after the desired temperature was attained indicating the instantaneous formation of the active catalytic species. The progress of the reaction was monitored by observing the pressure drop in the carbon monoxide reservoir. The reaction was continued till the pressure drop stopped completely. The reactor was then cooled and the liquid phase was analyzed by gas chromatography (GC). After 58 minutes, the GC analysis showed 79.4% conversion with 92.1% selectivity to acetic acid.

EXAMPLE 4

A 300 ml stirred autoclave was charged with the following compounds including the reactant and the catalyst components:

| | |
|---|---|
| Methanol | 0.5 moles |
| Methyl iodide | 0.08 moles |
| Ni(OAc)$_2$.4H$_2$O | 0.0084 moles |
| Thianthrene | 0.0336 moles |
| Water | 0.166 moles |
| Acetic acid (solvent) | 1.25 moles |

The contents of the autoclave were flushed with nitrogen and then with carbon monoxide. The contents were heated to 225° C. and the autoclave was pressurized with hydrogen (5% of total pressure) and carbon monoxide to a total pressure of 1000 psig. The pressure in the autoclave was maintained constant at 1000 psig by supplying only carbon monoxide from reservoir. In this instance also, carbon monoxide absorption commenced immediately indicating instantaneous formation of the active catalyst species. The progress of the reaction was monitored by observing the pressure drop in the carbon monoxide reservoir. The reaction was continued till the pressure drop stopped completely. The reactor was then cooled and the liquid phase was analyzed by gas chromatography (GC). After 200 minutes, the GC analysis showed 89.08% conversion with 69.7% selectivity to acetic acid.

EXAMPLE 5

A 300 ml stirred autoclave was charged with the following compounds including the reactant and the catalyst components:

| | |
|---|---|
| Methanol | 0.5 moles |
| Methyl iodide | 0.08 moles |
| Ni(OAc)$_2$.4H$_2$O | 0.0084 moles |
| 1,4-dithiane | 0.0336 moles |
| Water | 0.166 moles |
| Acetic acid (solvent) | 1.25 moles |

The contents of the autoclave were flushed with nitrogen and then with carbon monoxide. The contents were heated to 225° C. and the autoclave was pressurized with hydrogen (5% of total pressure) and carbon monoxide to a total pressure of 1000 psig. The pressure in the autoclave was maintained constant at 1000 psig by supplying only carbon monoxide from reservoir. In this instance also, carbon monoxide absorption commenced immediately indicating instantaneous formation of the active catalyst species. The progress of the reaction was monitored by observing the pressure drop in the carbon monoxide reservoir. The reaction was continued till the pressure drop stopped completely. The reactor was then cooled and the liquid phase was analyzed by gas chromatography (GC). After 280 minutes, the GC analysis showed 84.88% conversion with 85.98% selectivity to acetic acid.

EXAMPLE 6

A 300 ml stirred autoclave was charged with the following compounds including the reactant and the catalyst components:

| | |
|---|---|
| Methanol | 0.5 moles |
| Methyl iodide | 0.08 moles |

| | |
|---|---|
| Ni(OAc)$_2$.4H$_2$O | 0.0084 moles |
| 2-mercapto pyridine | 0.0336 moles |
| Water | 0.166 moles |
| Acetic acid (solvent) | 1.25 moles |

The contents of the autoclave were flushed with nitrogen and then with carbon monoxide. The contents were heated to 225° C. and the autoclave was pressurized with hydrogen (5% of total pressure) and carbon monoxide to a total pressure of 1000 psig. The pressure in the autoclave was maintained constant at 1000 psig by supplying only carbon monoxide from reservoir. In this instance also, carbon monoxide absorption commenced immediately indicating instantaneous formation of the active catalyst species. The progress of the reaction was monitored by observing the pressure drop in the carbon monoxide reservoir. The reaction was continued till the pressure drop stopped completely. The reactor was then cooled and the liquid phase was analyzed by gas chromatography (GC). After 98 minutes, the GC analysis showed 93.95% conversion with 72.81% selectivity to acetic acid.

EXAMPLE 7

A 300 ml stirred autoclave was charged with the following compounds including the reactant and the catalyst components:

| | |
|---|---|
| Methanol | 0.5 moles |
| Methyl iodide | 0.08 moles |
| Ni(OAc)$_2$.4H$_2$O | 0.0084 moles |
| 1,2-ethanedthiol | 0.0336 moles |
| Water | 0.166 moles |
| Acetic acid (solvent) | 1.25 moles |

The contents of the autoclave were flushed with nitrogen and then with carbon monoxide. The contents were heated to 225° C. and the autoclave was pressurized with hydrogen (5% of total pressure) and carbon monoxide to a total pressure of 1000 psig. The pressure in the autoclave was maintained constant at 1000 psig by supplying only carbon monoxide from reservoir. In this instance also, carbon monoxide absorption commenced immediately indicating instantaneous formation of the active catalyst species. The progress of the reaction was monitored by observing the pressure drop in the carbon monoxide reservoir. The reaction was continued till the pressure drop stopped completely. The reactor was then cooled and the liquid phase was analyzed by gas chromatography (GC). After 100 minutes, the GC analysis showed 97.40% conversion with 61.59% selectivity to acetic acid.

EXAMPLE 8

A 300 ml stirred autoclave was charged with the following compounds including the reactant and the catalyst components:

| | |
|---|---|
| Methanol | 0.5 moles |
| Lithium iodide | 0.08 moles |
| Ni(OAc)$_2$.4H$_2$O | 0.0084 moles |
| Morpholine | 0.0336 moles |
| Water | 0.166 moles |
| Acetic acid (solvent) | 1.25 moles |

The contents of the autoclave were flushed with nitrogen and then with carbon monoxide. The contents were heated to 225° C. and the autoclave was pressurized with hydrogen (5% of total pressure) and carbon monoxide to a total pressure of 1000 psig. The pressure in the autoclave was maintained constant at 1000 psig by supplying only carbon monoxide from reservoir. In this instance also, carbon monoxide absorption commenced immediately indicating instantaneous formation of the active catalyst species. The progress of the reaction was monitored by observing the pressure drop in the carbon monoxide reservoir. The reaction was continued till the pressure drop stopped completely. The reactor was then cooled and the liquid phase was analyzed by gas chromatography (GC). After 120 minutes, the GC analysis showed 89.2% conversion with 95.2% selectivity to acetic acid.

EXAMPLE 9

A 300 ml stirred autoclave was charged with the following compounds including the reactant and the catalyst components:

| | |
|---|---|
| Ethanol | 0.5 moles |
| Ethyl iodide | 0.08 moles |
| Ni(OAc)$_2$.4H$_2$O | 0.0084 moles |
| Morpholine | 0.0336 moles |
| Water | 0.166 moles |
| Acetic acid (solvent) | 1.25 moles |

The contents of the autoclave were flushed with nitrogen and then with carbon monoxide. The contents were heated to 225° C. and the autoclave was pressurized with hydrogen (5% of total pressure) and carbon monoxide to a total pressure of 1000 psig. The pressure in the autoclave was maintained constant at 1000 psig by supplying only carbon monoxide from reservoir. In this instance also, carbon monoxide absorption commenced immediately indicating instantaneous formation of the active catalyst species. The progress of the reaction was monitored by observing the pressure drop in the carbon monoxide reservoir. The reaction was continued till the pressure drop stopped completely. The reactor was then cooled and the liquid phase was analyzed by gas chromatography (GC). After 50 minutes, the GC analysis showed 96.4% conversion with 96.6% selectivity to propionic acid.

EXAMPLE 10

A 300 ml stirred autoclave was charged with the following compounds including the reactant and the catalyst components:

| | |
|---|---|
| Methanol | 0.5 moles |
| Methyl iodide | 0.08 moles |
| Ni(OAc)$_2$.4H$_2$O | 0.0084 moles |
| Morpholine | 0.0336 moles |

-continued

| | |
|---|---|
| Water | 0.166 moles |
| Acetic acid (solvent) | 1.25 moles |

The contents of the autoclave were flushed with nitrogen and then with carbon monoxide. The contents were heated to 225° C. and the autoclave was pressurized with hydrogen (5% of total pressure) and carbon monoxide to a total pressure of 1000 psig. The pressure in the autoclave was maintained constant at 1000 psig by supplying only carbon monoxide from reservoir. In this instance also, carbon monoxide absorption commenced immediately indicating instantaneous formation of the active catalyst species. The progress of the reaction was monitored by observing the pressure drop in the carbon monoxide reservoir. The reaction was continued till the pressure drop stopped completely. The reactor was then cooled and the liquid phase was analyzed by gas chromatography (GC). After 62 minutes, the GC analysis showed 70.16% conversion with 96.1% selectivity to acetic acid.

EXAMPLE 11

A 300 ml stirred autoclave was charged with the following compounds including the reactant and the catalyst components:

| | |
|---|---|
| Methanol | 0.5 moles |
| Methyl iodide | 0.08 moles |
| Ni(OAc)$_2$.4H$_2$O | 0.0084 moles |
| Morpholine | 0.0336 moles |
| Water | 0.166 moles |
| Acetic acid (solvent) | 1.25 moles |

The contents of the autoclave were flushed with nitrogen and then with carbon monoxide. The contents were heated to 225° C. and the autoclave was pressurized with hydrogen (5% of total pressure) and carbon monoxide to a total pressure of 1000 psig. The pressure in the autoclave was maintained constant at 1000 psig by supplying only carbon monoxide from reservoir. The progress of the reaction was monitored by observing the pressure drop in the carbon monoxide reservoir.

To test the catalyst stability, fresh methanol was added. The reaction was continued to check the activity of the catalyst. When the carbon monoxide absorption of approximately 80% was observed, fresh lot of methanol was added. This procedure was repeated four times. After 470 minutes, the GC analysis showed 89.2% conversion with 90.6% selectivity to acetic acid indicating that the catalyst activity was consistent accounting for dilution due to change in the volume.

ADVANTAGES OF THE INVENTION

1. The catalyst system of the invention is inexpensive compared to the iridium or rhodium catalysts of the prior art.
2. The combined effect of the nickel catalyst, iodide promoter, and heterocyclic organic compound show good activity and selectivity for the carboxylic acid.

We claim:
1. A process for the preparation of a carboxylic acid from the corresponding aliphatic alcohol, said process comprising reacting a nickel source, an iodide source, and a ligand or promoter in a solvent under carbon monoxide atmosphere to obtain an in situ catalyst complex, contacting a mixture of aliphatic alcohol and carbon monoxide with said catalyst complex at a temperature in the range of 100 to 400° C. and a pressure in the range of 5 to 3000 psig, for a minimum of 30 minutes, and separating the product obtained, and wherein the ligand or promoter comprises a heterocyclic organic compound containing at least two heteroatoms of which at least one is selected from S— and N—, and wherein the heterocyclic compound is selected from the group consisting of morpholine, 1,4 thioxane, 2,2'bithiophene, thiamorpholine, thianthrene, 1,4 dithiane, 1,2-ethaneditiol and 2-mercapto pyridine.

2. A process as claimed in claim 1 wherein the aliphatic alcohol comprises an aliphatic alcohol with 1 to 4 carbon atoms.

3. A process as claimed in claim 1 wherein the nickel source is selected from nickel, nickel salt and nickel powder.

4. A process as claimed in claim 3 wherein said nickel salt is selected from the group consisting of nickel chloride, nickel acetate, nickel bromide and nickel iodide.

5. A process as claimed in claim 1 wherein the iodide source is selected from the group consisting of alkyl iodide, hydroiodic acid and alkali metal iodide.

6. A process as claimed in claim 5 wherein the alkyl iodide comprises methyl iodide.

7. A process as claimed in claim 5 wherein the alkali metal iodide is selected from the group consisting of lithium iodide, sodium iodide and cesium iodide.

8. A process as claimed in claim 1 wherein the catalyst complex is of the general formula $A_lB_mC_n$, wherein A is nickel, B is the ligand or promoter, C is the iodide source, l is the mole percentage of nickel and is in the range of 1 to 25, m is the mole percentage of ligand or promoter and is in the range of 5 to 50, and n is the mole percentage of the iodide source, such that m/l=2 to 8 and l+m+n=100.

9. A process as claimed in claim 1 wherein the solvent used comprises an aliphatic carboxylic acid.

10. A process as claimed in claim 8 wherein the aliphatic carboxylic acid is selected from the group consisting of acetic acid, propionic acid and butyric acid.

11. A process as claimed in claim 1 wherein the mole ratio of the solvent to the alcohol is in the range of 0.5 to 10.

12. A process as claimed in claim 1 wherein the carbonylation reaction is carried out in the presence of water and hydrogen.

13. A process as claimed in claim 12 wherein the amount of water is in the range of 5 to 10% of the total charge.

14. A process as claimed in claim 12 wherein the ratio of carbon monoxide to hydrogen in the pressurizing gas is from 1 to 40.

15. A process as claimed in claim 1 wherein the aliphatic alcohol used is methanol to obtain acetic acid and methyl acetate.

16. A process as claimed in claim 1 wherein the aliphatic alcohol used is ethanol to obtain propionic acid and ethyl propionate.

17. A process as claimed in claim 1 wherein the iodide source and the carboxylic acid product are separated from the catalyst composite at the end of the reaction.

18. A process as claimed in claim 1 wherein the iodide source and the carboxylic acid product are separated from the catalyst composite by distillation.

19. A process as claimed in claim 1 wherein the catalyst and the iodide source are recycled from additional use.

20. A process as claimed in claim 12 wherein the ratio of carbon monoxide to hydrogen in the pressurizing gas is from 1 to 30.

21. A process for the preparation of a carboxylic acid from the corresponding aliphatic alcohol, said process comprising reacting a nickel source, an iodide source, and a ligand or promoter in a solvent under carbon monoxide atmosphere to obtain an in situ catalyst complex, contacting a mixture of aliphatic alcohol and carbon monoxide with said catalyst complex at a temperature in the range of 100 to 400° C. and a pressure in the range of 5 to 3000 psig, for a minimum of 30 minutes, and separating the product obtained, and wherein the ligand or promoter does not include any trivalent N compounds.

22. A process for the preparation of a carboxylic acid from the corresponding aliphatic alcohol, said process comprising reacting a nickel source, an iodide source, and a ligand or promoter in a solvent under carbon monoxide atmosphere to obtain an in situ catalyst complex, contacting a mixture of aliphatic alcohol and carbon monoxide with said catalyst complex at a temperature in the range of 100 to 400° C. and a pressure in the range of 5 to 3000 psig, for a minimum of 30 minutes, and separating the product obtained, and wherein the ligand or promoter comprises a heterocyclic organic compound containing at least two heteroatoms of which at least one is selected from S— and N—, and wherein the catalyst complex is of the general formula $A_l B_m C_n$, wherein A is nickel, B is the ligand or promoter, C is the iodide source, l is the mole percentage of nickel and is in the range of 1 to 25, m is the mole percentage of ligand or promoter and is in the range of 5 to 50, and n is the mole percentage of the iodide source, such that m/l=2 to 8 and l+m+n=100.

23. A process as claimed in claim 22 wherein the aliphatic alcohol comprises an aliphatic alcohol with 1 to 4 carbon atoms.

24. A process as claimed in claim 22 wherein the nickel source is selected from nickel, nickel salt and nickel powder.

25. A process as claimed in claim 24 wherein said nickel salt is selected from the group consisting of nickel chloride, nickel acetate, nickel bromide and nickel iodide.

26. A process as claimed in claim 22 wherein the iodide source is selected from the group consisting of alkyl iodide, hydroiodic acid and alkali metal iodide.

27. A process as claimed in claim 26 wherein the alkyl iodide comprises methyl iodide.

28. A process as claimed in claim 26 wherein the alkali metal iodide is selected from the group consisting of lithium iodide, sodium iodide and cesium iodide.

29. A process as claimed in claim 22 wherein the heterocyclic compound is selected from the group consisting of morpholine, 1,4 thioxane, 2,2'bithiophene, thiamorpholine, thianthrene, 1,4 dithiane, 1,2-ethaneditiol and 2-mercapto pyridine.

30. A process as claimed in claim 22 wherein the solvent used comprises an aliphatic carboxylic acid.

31. A process as claimed in claim 22 wherein the aliphatic carboxylic acid is selected from the group consisting of acetic acid, propionic acid and butyric acid.

32. A process as claimed in claim 22 wherein the mole ratio of the solvent to the alcohol is in the range of 0.5 to 10.

33. A process as claimed in claim 22 wherein the carbonylation reaction is carried out in the presence of water and hydrogen.

34. A process as claimed in claim 33 wherein the amount of water is in the range of 5 to 10% of the total charge.

35. A process as claimed in claim 33 wherein the ratio of carbon monoxide to hydrogen in the pressurizing gas is from 1 to 40.

36. A process as claimed in claim 22 wherein the aliphatic alcohol used is methanol to obtain acetic acid and methyl acetate.

37. A process as claimed in claim 22 wherein the aliphatic alcohol used is ethanol to obtain propionic acid and ethyl propionate.

38. A process as claimed in claim 22 wherein the iodide source and the carboxylic acid product are separated from the catalyst composite at the end of the reaction.

39. A process as claimed in claim 22 wherein the iodide source and the carboxylic acid product are separated from the catalyst composite by distillation.

40. A process as claimed in claim 22 wherein the catalyst and the iodide source are recycled from additional use.

41. A process as claimed in claim 33 wherein the ratio of carbon monoxide to hydrogen in the pressurizing gas is from 1 to 30.

* * * * *